US009149172B2

(12) United States Patent
Iddan et al.

(10) Patent No.: US 9,149,172 B2
(45) Date of Patent: Oct. 6, 2015

(54) SYSTEM AND APPARATUS FOR ANCHORING AND OPERATION OF IN-VIVO MEDICAL DEVICES

(71) Applicant: GIVEN IMAGING LTD., Yoqneam (IL)

(72) Inventors: Gavriel J. Iddan, Haifa (IL); Zvika Gilad, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 236 days.

(21) Appl. No.: 13/726,852

(22) Filed: Dec. 26, 2012

(65) Prior Publication Data

US 2013/0172672 A1   Jul. 4, 2013

Related U.S. Application Data

(60) Provisional application No. 61/581,569, filed on Dec. 29, 2011.

(51) Int. Cl.
*A61B 1/04* (2006.01)
*A61B 1/06* (2006.01)
*A61B 1/00* (2006.01)

(52) U.S. Cl.
CPC ......... *A61B 1/00158* (2013.01); *A61B 1/00147* (2013.01); *A61B 1/041* (2013.01)

(58) Field of Classification Search
CPC ............... A61B 1/041; A61B 1/00147; A61B 1/00158; A61B 5/6879; A61B 5/6882; A61B 5/6883; A61B 5/6884; A61B 5/6885; A61B 5/6886

USPC .................. 600/109, 117, 118, 160, 104, 106
See application file for complete search history.

(56) References Cited

U.S. PATENT DOCUMENTS

| | | | | |
|---|---|---|---|---|
| 5,604,531 | A * | 2/1997 | Iddan et al. | 348/76 |
| 6,285,897 | B1 | 9/2001 | Kilcoyne | |
| 6,530,933 | B1 * | 3/2003 | Yeung et al. | 606/151 |
| 6,689,056 | B1 * | 2/2004 | Kilcoyne et al. | 600/300 |
| 7,654,985 | B2 | 2/2010 | Dinsmoor | |
| 7,946,979 | B2 | 5/2011 | Gilad | |
| 8,323,192 | B2 | 12/2012 | Kilcoyne | |
| 2002/0042562 | A1 | 4/2002 | Meron | |
| 2003/0167000 | A1 * | 9/2003 | Mullick et al. | 600/424 |

(Continued)

FOREIGN PATENT DOCUMENTS

WO   WO 2011/072060   6/2011

*Primary Examiner* — Anhtuan T Nguyen
*Assistant Examiner* — William Chou
(74) *Attorney, Agent, or Firm* — Pearl Cohen Zedek Latzer Baratz LLP

(57) ABSTRACT

In-vivo medical devices, systems and methods of operating such devices include a permanent magnetic assembly interacting with external magnetic fields for magnetically maneuvering said device to a desired location along a patient's GI tract, and anchoring said devices to the desired location for a period of time. The in-vivo medical device includes illumination sources, an optical system, and an image sensor for imaging the GI tract and thus assisting in locating the desired location. Some in-vivo medical devices include a concave window, which enables better imaging of small areas along the tissue. Furthermore, in-vivo devices with a concave window enable carrying operating tools without damaging the tissue of the GI tract, since prior to operation, the tools protrude from the concave window but remain behind the ends of the edges of the concave window.

17 Claims, 13 Drawing Sheets

(56) References Cited

U.S. PATENT DOCUMENTS

| | | | |
|---|---|---|---|
| 2004/0030454 A1* | 2/2004 | Kim et al. | 700/245 |
| 2004/0133089 A1 | 7/2004 | Kilcoyne | |
| 2005/0038370 A1* | 2/2005 | Kuth et al. | 602/78 |
| 2005/0143624 A1 | 6/2005 | Iddan | |
| 2005/0177069 A1* | 8/2005 | Takizawa et al. | 600/573 |
| 2006/0004255 A1 | 1/2006 | Gilad | |
| 2006/0193505 A1* | 8/2006 | Glukhovsky et al. | 382/128 |
| 2008/0091177 A1 | 4/2008 | Christian | |
| 2008/0312502 A1 | 12/2008 | Swain | |
| 2010/0217368 A1 | 8/2010 | Dinsmoor | |
| 2011/0166416 A1* | 7/2011 | Katayama et al. | 600/104 |
| 2011/0207998 A1* | 8/2011 | Katayama | 600/106 |

\* cited by examiner

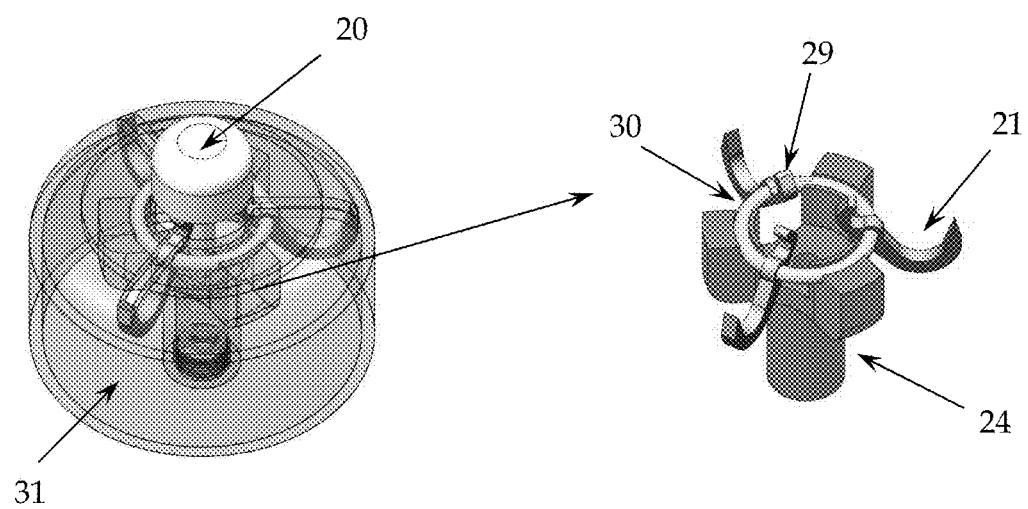
Fig. 8A                    Fig. 8B

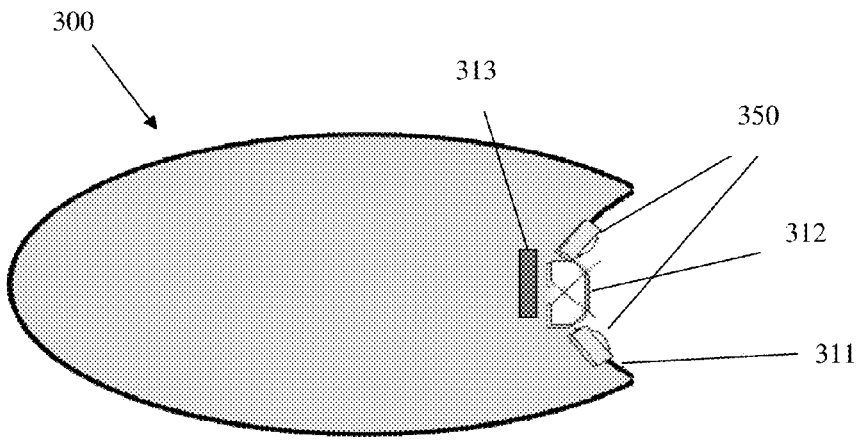
Fig. 12
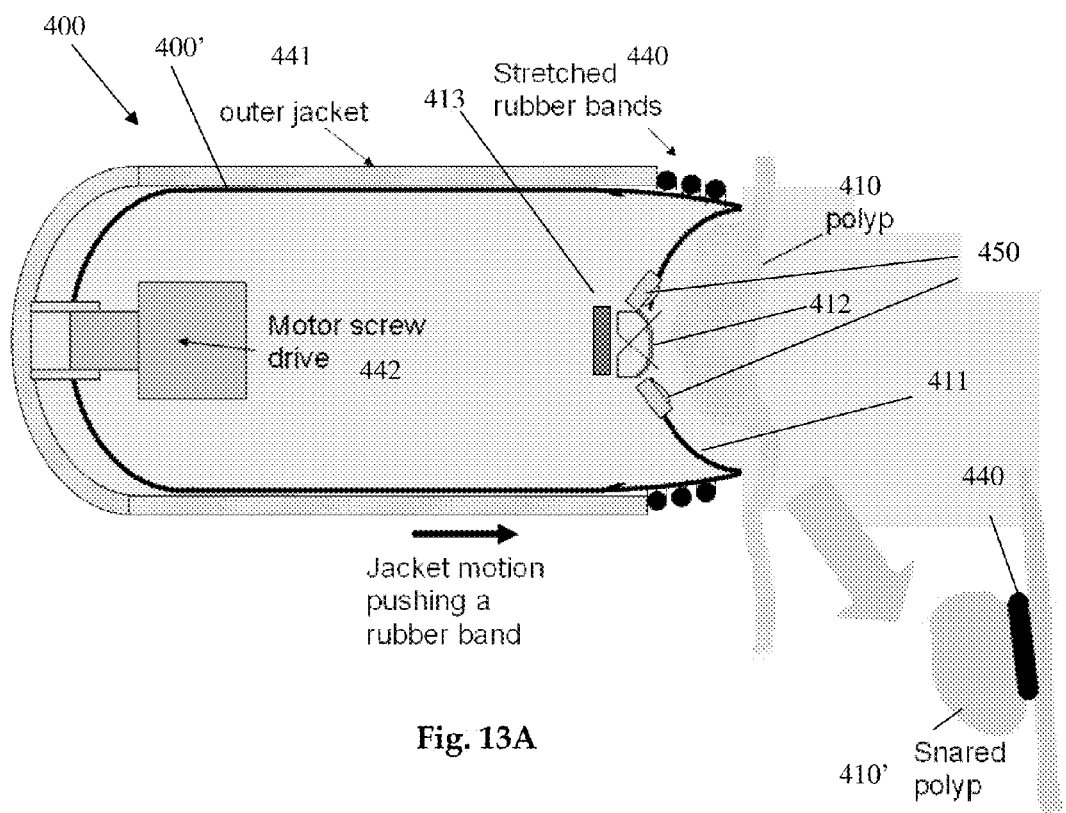
Fig. 13A
Fig. 13B

SYSTEM AND APPARATUS FOR ANCHORING AND OPERATION OF IN-VIVO MEDICAL DEVICES

FIELD OF THE INVENTION

The present invention relates to fully controlled (maneuvered) in-vivo medical devices containing special anchoring and/or treatment mechanisms. The invention further relates to systems, apparatus and methods for anchoring and operating said devices.

BACKGROUND OF THE INVENTION

Fully autonomous in-vivo devices for the diagnostic and/or imaging of the gastrointestinal (GI) tract, such as the Pill-Cam® capsule endoscopes, are propelled by natural peristaltic forces and thus pass naturally in the body while delivering data collected therein, including, for example, images, to an external receiver. However, the physician has no control over the motion of these autonomous medical devices. As a result, for instance, an autonomous in-vivo imaging device may have to acquire a large number of images as it traverses the GI tract, many of which are not images of pathological regions of interest, just to be able to acquire among them images of a pathological regions of interest. The surplus images may deplete the device's energy source and extend the time required by a user for browsing and sorting the images.

The uncontrolled motion of the autonomous in-vivo medical device may become a problem when longer observation, diagnostics and treatment of a specific location along the GI tract is desired. The physician might not wish to fully rely upon the natural peristaltic forces that are uncontrollable by an operator.

Thus, holding the in-vivo device at a desired location for a certain period of time may be critical for definitive diagnosis and/or treatment of various pathological areas.

The U.S. Pat. No. 7,946,979, which is entitled "Immobilizable In-Vivo Sensing Device" and assigned to the common assignee of the present invention, describes an in-vivo device that is anchored to the lower esophagus by a special pin and monitors the reflux for a few days. The pinned tissue becomes necrotic after a few days, and the in-vivo device detaches itself from the esophagus and is naturally discharged.

The U.S. Patent Application Publication No. 2005/0143624, which is entitled "Immobilizable In-Vivo Imager with Moveable Focusing mechanism" and also assigned to the common assignee of the present invention, relates to a system, method and device for immobilizing an imager in-vivo and/or focusing images on the imager reflected from an in-vivo site to be monitored. The device described in the above publication may include one or more immobilizing units, such as rotatable clasps, a gluing tube and vacuum pads, that may hold or secure the device to endolumenal surfaces, for example.

A further example of an immobilized in-vivo sensing device that can be used, for example, for monitoring imaging or biliary manipulations, and liver biopsy without the use of a conventional laparoscopy and imaging of subhepatic structures inaccessible to laparoscopy, is described in the U.S. Patent Application Publication No. 2008/0312502, which is assigned to the common assignee of the present invention. The publication suggests using the transabdominal and peritoneal attachment methods for immobilization of the in-vivo device.

The U.S. Patent Application Publications No. 2006/0004255, entitled "In-Vivo Sensing System", and No. 2002/0042562, entitled "Immobilizable In-Vivo Sensing Device", both assigned to the common assignee of the present invention, suggest affixing the housing of the in-vivo device by way of, for example, clasps. Constituents such as fasteners, glue, thread or fiber attached to the housing with one or more rings or indentations may be used. The publications also suggest using anchors to attach the device to an internal body tissue. The anchors, which typically extend from the housing of the device, may include fasteners, which grasp the body tissue. The fasteners, such as for example, pins, screws, suction cups, or clasps, may hold on to a section of the tissue by, for example, slightly piercing or pinching the tissue, through suction.

The above mentioned anchoring mechanisms, however, may risk damage to tissue or may encounter a problem of obstruction of the device in the GI tract in the event of its malfunction.

SUMMARY OF THE INVENTION

The aforementioned problems of holding the in-vivo device at a desired location for a certain period of time, while avoiding the risk of damaging or obstructing the GI tract, may be solved by using an in-vivo medical device comprising new anchoring mechanisms for attaching the device to a certain desired location where the pathology is detected and treatment is required or needed. It is, therefore, an object of the present invention to provide methods for anchoring the in-vivo medical devices. Another object is to provide the in-vivo medical devices comprising various anchoring mechanisms or apparatus for immobilizing the device in the areas of the pathological lesions.

Furthermore, it is another object of the present invention to provide in-vivo medical devices comprising a unique optical design that enables better imaging and operation of various tools carried by the device, while avoiding risk of damaging or obstructing the GI tract when the tools are not in use.

Various embodiments of the invention provide an in-vivo medical device comprising the anchoring mechanism and methods for anchoring said in-vivo medical device.

In one embodiment, the in-vivo medical device may be a swallowable maneuverable capsule, which, for example, may detect and treat pathologies during its passage through the GI tract.

According to a particular embodiment, the in-vivo medical device may be fully controlled, including maneuvering the device to a desired location and/or orientation of the device in the GI tract, and maintaining its location and orientation for as long as the docking procedure is required. This fully controlled in-vivo device may contain an assembly of permanent magnets in order to interact with external magnetic fields for generating forces for steering the device.

In addition, the in-vivo device may include a multilayered imaging and sensing printed circuit board (PCB) for operating the device, e.g., sensing its current location and orientation, transmitting the respective location and orientation data to an external system that generates the external magnetic fields and steers the device. The internal components of the device may reside on the PCB, which may include a sensor for sensing the current location of the device, an antenna typically associated with a transmitter for transmitting data from the device to an external system, and other components of the device, such as conductive rings. Other designs, components, elements, and structures may be used in addition to and/or in place of the rings, steps, etc. The PCB may further include contact points to connect additional components.

In some embodiments, the fully controlled in-vivo medical device may be positioned at the desired location using an external magnetic field. The device may then be anchored for a desired time period even when the external magnetic field has been terminated. In other embodiments, the fully controlled in-vivo medical device may be positioned and held at a desired location using the external magnetic field so that various tools may be operated even without anchoring the device to the tissue.

The in-vivo device may be anchored to the walls of the GI tract in a specific area where the pathology is detected and the treatment is required, using various anchoring mechanisms triggered either externally, by an operator, or internally, by an automatic signal that is transmitted from a force threshold sensor or a proximity sensor.

In one embodiment, the anchoring mechanism is based on activation of special grippers or anchors, which may or may not be biodegradable. The anchoring mechanisms, described hereinafter, may be of the following types: "earring" mechanism, "snap" mechanism, and "harpoon" mechanism.

According to one embodiment, operation of the "earring" mechanism may comprise the step of releasing a pre-stressed anchoring wire or earring catch when the in-vivo device is pressed against the walls of the GI tract. In a further embodiment, the device, which uses the earring mechanism, may contain an electromotor with the magnet control that operates the release of the earring catch.

In another embodiment, the "snap" mechanism may be based on a two-step process initiated by release of a special safety catch when the device is pressed against the walls of the GI tract. As a result, open grippers, which are initially held under tension of a spring, rapidly snap shut catching the tissue of the GI tract walls.

In a further embodiment, the "harpoon" mechanism may make use of a mini-harpoon, which is capable of piercing the GI tract tissue when the device is pressed against the walls of the GI tract and a special safety catch is released.

In yet another embodiment, the in-vivo medical device may comprise a sensor to identify the pathological area where the docking is required. The sensor may be a bleeding detection sensor or a pH sensor. In some embodiments, the sensor may indicate, for example, the entrance of the in vivo device into a region of interest, such as the small bowl.

In a further embodiment, the device may be assembled inside a case (shell or housing), which may optionally have a substantially transparent portion.

In one embodiment, the in-vivo medical device may be equipped with one or more illumination sources, e.g., LEDs in order to illuminate the desired locations inside the GI tract.

In yet a further embodiment, the device may additionally include an imager setup in order to acquire an in-vivo image of a body lumen, and a power source, such as batteries.

According to a specific embodiment, a system for anchoring the device may include the fully controlled medical in-vivo device, external rotatable magnets for steering the internal magnets of said device and thereby fully controlling its movement inside the GI tract, an external receiver/recorder able to receive data (e.g., image data) transmitted by the in-vivo device, and a computing platform or workstation able to steer and control the device, and to store, process, display or analyze the received data.

According to some embodiments, an in-vivo device may include a concave optical window instead of the conventional convex or dome shaped optical window. A concave window may enable setting the device close to a location of interest. A concave window may further enable better imaging of small areas along the tissue, since the device may be positioned closer to the tissue than when the device includes a convex window, which may be used to push the tissue away from the device's imager. Furthermore, operating tools may be easily carried by an in-vivo device that includes a concave window, without the tools damaging the tissue of the GI tract. In case of failure of the tools to retract into the device's housing at the end of a procedure performed by the tools, the concave window may prevent the tools from getting close to the tissue, since the tools remain behind the ends of the edges of the concave window.

In some embodiments, a method for anchoring the in-vivo medical device includes the following steps:
  inserting into a patient a fully controlled in-vivo medical device;
  controlling the movement of said device inside the GI tract by manipulating external magnets in close proximity to the patient;
  positioning the device at the desired location along the GI tract, where the in-vivo diagnosis or treatment is desired; and
  anchoring the device to the tissue walls of the GI tract in order to perform the diagnosis or treatment for a certain period of time.

The method may further optionally include acquiring in-vivo images of the body lumen; transmitting the acquired in-vivo images or other data; analyzing the in-vivo images or data; and/or other suitable operations.

Various embodiments of the invention may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The present invention will be understood and appreciated more fully from the following detailed description taken in conjunction with the appended figures. Various exemplary embodiments are well illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIG. 8A is a perspective view of the "snap" mechanism, in accordance with an embodiment of the present invention;

FIG. 8B is a perspective view of the "snap" mechanism without its chamber cover, in accordance with an embodiment of the present invention;

FIG. 12 illustrates a schematic view of an in-vivo medical device comprising a concave window, in accordance with a second embodiment of the present invention;

FIGS. 13A-B illustrate a schematic view of an in-vivo medical device comprising a concave window, and the tissue following operation of the device, respectively, in accordance with a third embodiment of the present invention.

Figure 1A:
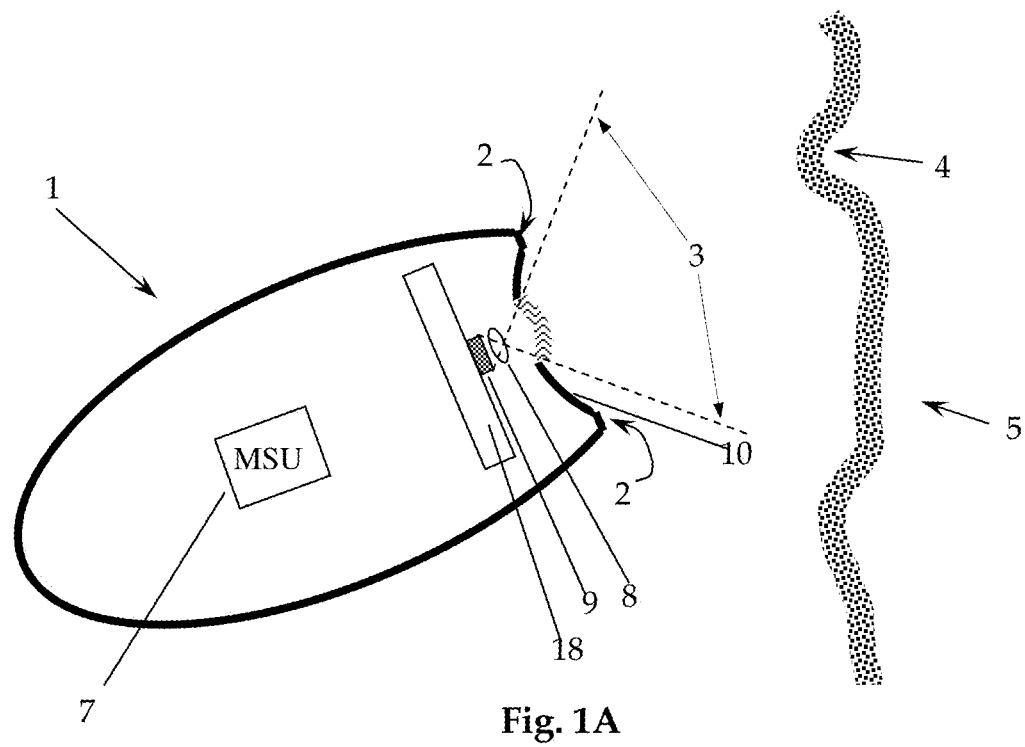
FIG. 1A is a schematic view of an in-vivo medical device approaching the pathological lesion in the GI tract tissue, in accordance with an embodiment of the present invention.

It will be appreciated that for simplicity and clarity of illustration, elements shown in the figures have not necessarily been drawn to scale. For example, the dimensions of some of the elements may be exaggerated relative to other elements for clarity. Furthermore, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

It should be noted that although a portion of the discussion may relate to fully controlled in-vivo diagnostic and therapeutic medical devices, systems and methods, the present invention is not limited in this regard, and embodiments of the present invention may be used in conjunction with various other in-vivo sensing and imaging devices, systems, and methods. As such, some embodiments of the invention may be used, for example, in conjunction with autonomous in-vivo sensing devices for testing pH, temperature, pressure and/or electrical impedance, in-vivo detection of a substance or a material, in-vivo detection and imaging of strictures or other medical conditions or pathology, in-vivo acquisition or analysis of data, and/or various other in-vivo sensing and imaging devices, systems, and methods. Some embodiments of the invention may be used not necessarily in the context of in-vivo imaging or in-vivo sensing. For example, embodiments of the invention may be used in devices for in-vivo treatment and therapy, such as an in-vivo device configured to release a medicament or to perform biopsy or surgery in vivo.

In one embodiment, the in-vivo medical device may typically be self-contained. For example, the in-vivo device according to some embodiments may be a capsule or other unit where all the components are substantially contained within a case or shell of the device, and where the device does not require wires or cables in order to receive power or transmit information, for example.

The in-vivo device according to one embodiment may be designed to access pathologic lesions in nearly every region of the gastrointestinal (GI) tract, including the colon and biliary tree. In some embodiments, the in-vivo device may be designed to collect the samples in the pathological areas only and to bypass the healthy areas, and it may be designed to access difficult to reach areas, where tethered endoscopes cannot reach or cannot reach easily.

Some embodiments of the present invention are directed to a typically swallowable in-vivo medical device in a form of a swallowable capsule that may be used for diagnosing and treating the pathological areas inside the GI tract.

In general, components of the device according to embodiments of the present invention may be similar to components used in the PillCam® capsule endoscopy system commercially available from Given Imaging Ltd., Yoqneam, Israel, the common assignee of the present invention. Of course, devices, systems, structures, functionalities and methods as described herein may have other configurations, sets of components and processes, etc.

While a device, system and method in accordance with embodiments of the invention may be used, for example, in a human body, the invention is not limited in this respect. For example, some embodiments of the invention may be used in conjunction with or inserted into a non-human body, e.g., a dog, a cat, a rat, a cow, or other animals, pets, laboratory animals, etc.

Figure 1B:
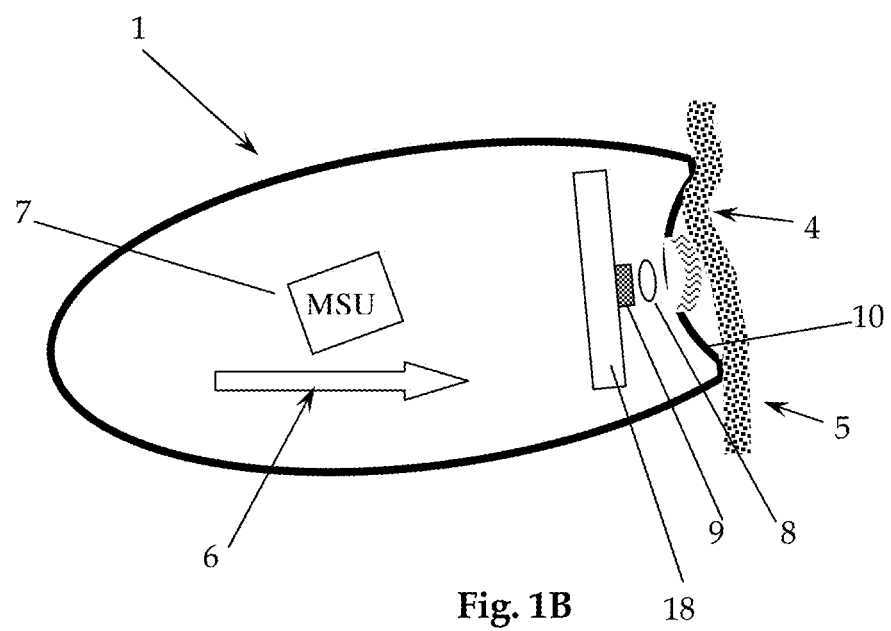
FIG. 1B is a schematic view of an in-vivo medical device positioned against the GI tract tissue to be treated or diagnosed, in accordance with another embodiment of the present invention.

Reference is now made to FIGS. 1A and 1B, which schematically show in-vivo medical device 1 approaching a pathological lesion 4 in the GI tract tissue 5, and docking against the tissue to be treated, respectively, in accordance with one embodiment of the present invention. The device 1 may be maneuvered inside the body lumen by external magnetic fields in order to approach the desired pathological area, which may include, e.g., pathological lesion 4. Device 1 may comprise a concave window 10 that may enable a sensing or imaging mechanism within device 1 to come closer to a pathological area, e.g. lesion 4, than it would be able to with a convex window. Thus, concave window 10 may enable device 1 to acquire high quality in-vivo images of a pathology, containing more details than it would have if device 1 had a convex window, which forces a sensing or imaging mechanism within the device to remain at a distance from the tissue. Device 1 may acquire images using an image sensor 9, optical system 8 and possibly illumination sources (not shown) all operating through the concave window 10. In addition, concave window 10 may enable image sensor 9, optical system 8 and any illumination sources of device 1 to come close to a pathological area and may enable device 1 to be anchored around substantially the entire pathological area, thus enabling device 1 to perform diagnosis or treatment of that area for a certain period of time.

In a particular embodiment, the in-vivo therapeutic device 1 may be fully controlled including steering and maneuvering of said device 1 to a desired location and/or orientation of the device 1 in the GI tract, and maintaining the location/orientation for as long as the therapy or diagnosis of a particular location is required or needed. This in-vivo device 1 may include a permanent magnet assembly or magnetic steering unit 7 (hereinbelow, "MSU") for interacting with the external magnetic fields for generating forces for steering the device 1.

The MSU 7 of the in-vivo device 1 may sense two types of magnetic fields: one type of magnetic field for magnetically inducing location and/or orientation signals in the in-vivo device 1, and another type of magnetic field for magnetically inducing maneuvering forces for maneuvering the device 1. Steering of the device 1 may be controlled based on the location/orientation signals, as described in details in PCT Patent Application Publication No. WO 2011/072060 assigned to Magnetecs Corporation. MSU 7 of device 1 may include similar components to those described in FIG. 3A of WO 2011/072060, for example, permanent magnet 101, 102, radially magnetized permanent magnet 103 and silver disk 104, and its silver manifold 105, 106. These components are configured to rotate, translate, and levitate devices such as device 1 within a body cavity.

In addition, with regards to FIG. 14 of the aforementioned PCT application, the system for maneuvering the in-vivo device, may include a magnetic maneuvering unit (hereinbelow, "MMU") consisting of coils generating the magnetic fields that induce the location/orientation signals in the in-vivo device 1, for interpreting the location/orientation signals originating from the device 1, and for generating a magnetic field to steer the device 1 to a desired location/orientation.

For example, after the in-vivo medical device 1 is swallowed, it may start capturing images of the GI tract, generate an image frame for each captured image, and transmit the image frames to an external data recorder. The MMU takes control over the location and orientation of the in-vivo device 1 in the GI tract, whereas the MSU of the in-vivo device 1 uses an on-board sensing coil assembly to sense the magnetic fields, and returns a feedback to the MMU. In one embodiment, the in-vivo device 1 may transmit the location/orientation data embedded in the image frames. In another embodiment, the in-vivo device 1 may transmit the location/orientation data independently of the image frames, for example by using a separate or dedicated transmission circuit and/or separate communication channel.

Arrival at a desired location of in-vivo device 1 is schematically shown in FIG. 1A, as indicated by appearance of pathological lesion 4 in field of view 3 of the device's image sensor 9 (positioned on PCB 18). FIG. 1A shows that the in-vivo device 1 is stopped at a distance from pathological lesion 4 such that the lesion 4 may be viewed or sensed in more detail compared to its surroundings. In some embodiments, device 1 may further comprise illumination sources (not shown) in order to illuminate the pathological lesion 4, and thus imager 9 may acquire a better image of lesion 4 through optical system 8. The operator may recognize the images of pathological lesion 4 and may activate the MMU in order to orient the medical in-vivo device 1 towards the GI tract wall, thereby forcing the MSU 7 to steer the device 1 to come into contact with tissue 5, as shown in FIG. 1B.

Figure 2:
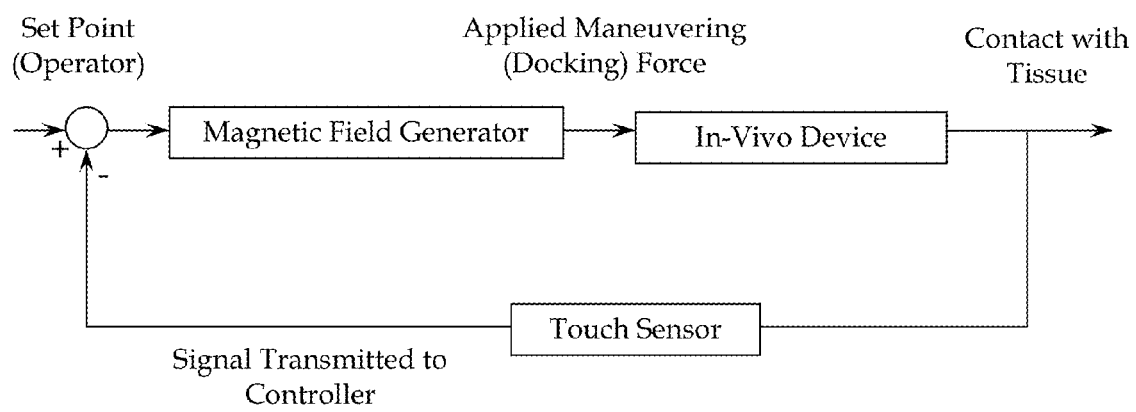
FIG. 2 is a diagram showing the closed loop positioning for docking force control, in accordance with an embodiment of the present invention.

In one embodiment, as shown in FIG. 1A, device 1 may comprise touch sensors 2. Touch sensors 2 may transmit the contact data to a control circuit, which is schematically shown in FIG. 2. A maneuvering (or positioning) force 6 shown on FIG. 1B, is induced by this control circuit, namely a closed loop positioning force control system. This maneuvering force 6 may constantly position the in-vivo device 1 against the surface of tissue 5 at a fixed relative position. In other words, the force 6 maintains the device in contact with the tissue for the length of the performed diagnostic or therapeutic procedure. The entire procedure may be monitored by the imager 9 of the device 1.

The closed loop positioning force control system shown on FIG. 2 has the advantage of being flexible, changeable and can be terminated at any time when so desired by an operator. As shown on FIG. 2, the maneuvering force 6 is fully controlled by the operator tuning the magnetic force generator in order to resist the peristaltic disturbances trying to push the in-vivo device off the desired location. Consequently, the in-vivo device 1 contacts the tissue 5, completing the positioning process. The touch sensors 2 serve as a feedback to the control circuit and may guarantee robust operation of the positioning procedure. There may be a closed loop between the magnetic force generator and the touch sensors 2, such that the force operating on the tissue remains substantially permanent. Thus, even if the tissue of the lumen moves due to peristaltic motion of the GI tract, device 1 will move in a direction corresponding to the movement of the tissue and at the corresponding amount in order to maintain a constant pressure between device 1 and the tissue, thereby maintaining constant contact between device 1 and the tissue.

The positioning of the in-vivo device 1 (10, 100, 1000 or any of the other devices described hereinafter) against the tissue 5 requires constant operation of the magnetic field generator, because if the magnetic field generator is disconnected, the device 1 may lose its contact with the tissue 5 and be moved away by peristaltic forces. In some embodiments of this invention, instead of applying a closed loop between the magnetic force generator and the touch sensors in order to maintain constant contact between device 1 and the tissue (as described above), the device 1 may achieve contact with the tissue by "docking" or "anchoring" the in-vivo device 1 to the walls of the GI tract.

The "anchoring" of the in-vivo device 1 is defined as the attachment or affixation of the in-vivo medical device 1 to a desired location in the GI tract for a desired period of time, for example, even when the maneuvering forces have been terminated. The anchoring requires an anchoring mechanism comprised within or connected to the in-vivo device 1.

In some embodiments, the anchoring mechanisms are triggered by an operator command or by an automatic signal transmitted from a force threshold sensor or a proximity sensor.

In one embodiment, the in-vivo medical device may be anchored to the tissue of the GI tract walls using three different anchoring mechanisms: "earring" mechanism, "snap" mechanism, and "harpoon" mechanism.

In a further embodiment, the above anchoring mechanisms are based on activation of special grippers or anchors, which may or may not be biodegradable.

Figure 3A:
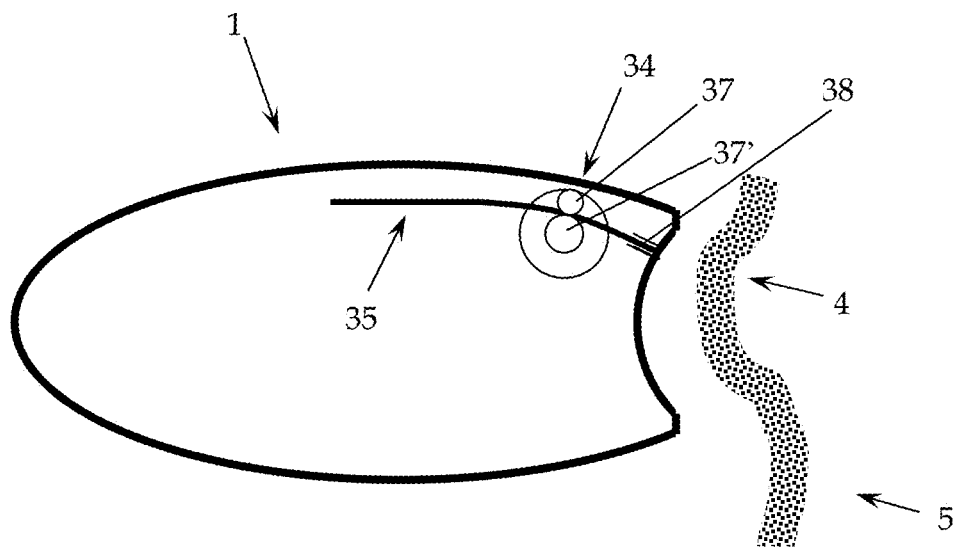
FIG. 3A is a schematic view of an in-vivo medical device comprising the "earring" mechanism before anchoring to the tissue of the GI tract wall, in accordance with an embodiment of the present invention.
Figure 3B:
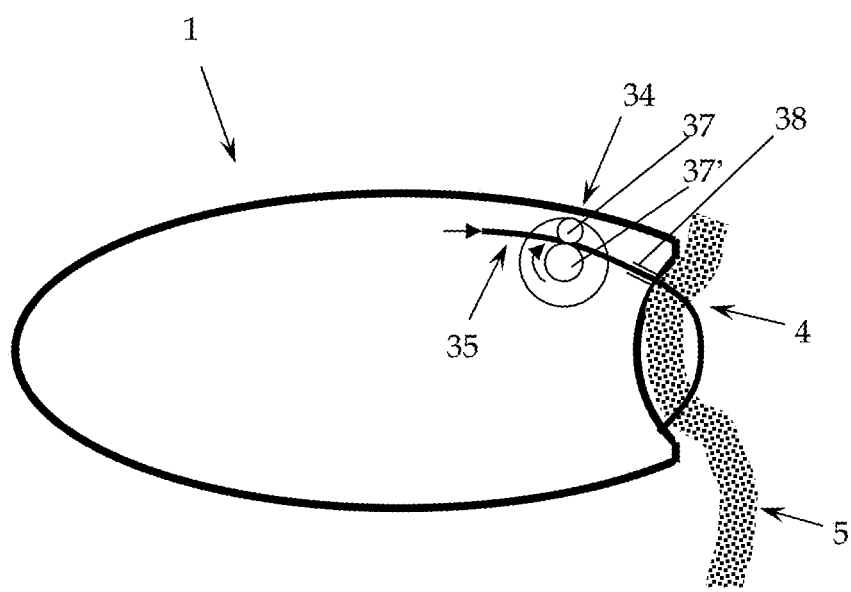
FIG. 3B is a schematic view of an in-vivo medical device comprising the "earring" mechanism after anchoring to the tissue of the GI tract wall, in accordance with an embodiment of the present invention.

Reference is now made to FIGS. 3A and 3B, which schematically show the in-vivo medical device 1 comprising the earring mechanism before and after the anchoring to the tissue of the GI tract wall, respectively, in accordance with an embodiment of the present invention. In a particular embodiment, operation of the earring mechanism comprises the step of releasing a pre-stressed anchoring wire, defined as earring catch 35, when the in-vivo device 1 is pressed against the GI tract walls. In yet a further embodiment, the in-vivo device 1, which uses the earring mechanism, may contain an electromotor 34 with the magnet control that operates the release of the earring catch 35. Electromotor 34 may comprise two wheels 37 and 37', which rotate one against the other in opposite directions. Once the wheels 37 and 37' rotate the wire or earring catch 35, earring catch 35 may be pushed forward towards opening 38. Earring catch 35 may be designed such that it bends as soon as it is pushed outside of device 1, through opening 38, when no pressure from the wheels 37 and 37' is applied onto it. Wire or earring catch 35 may be made of shape memory alloys, such as Nitinol, in order to retain a memory for the bent shape. Alternatively, wire or earring catch 35 may have this bent shape even while inside in-vivo device 1.

Figure 4A:
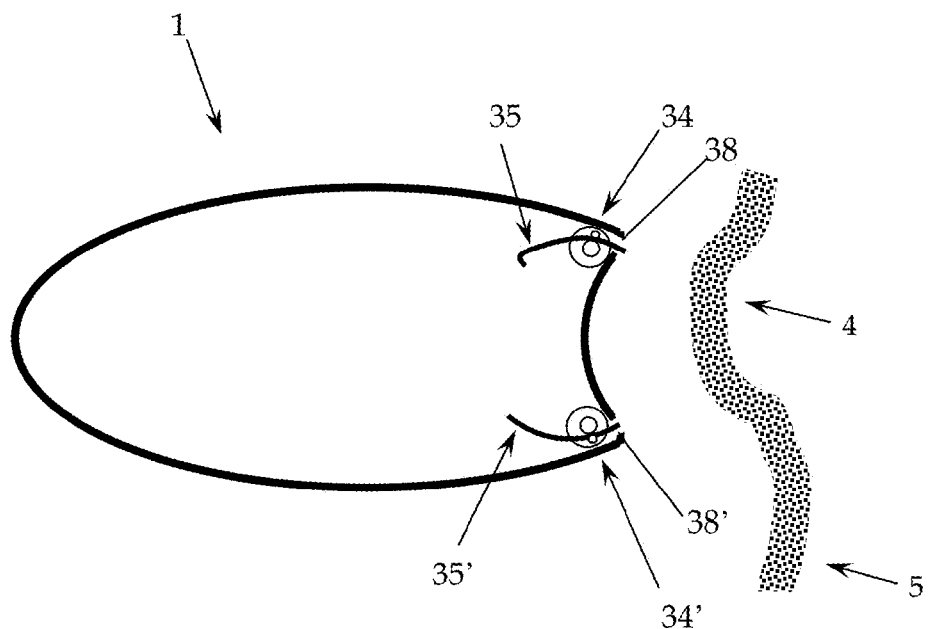
FIG. 4A is a schematic view of the in-vivo medical device comprising the two wires "earring" mechanism before anchoring to the tissue of the GI tract wall, in accordance with an embodiment of the present invention.
Figure 4B:
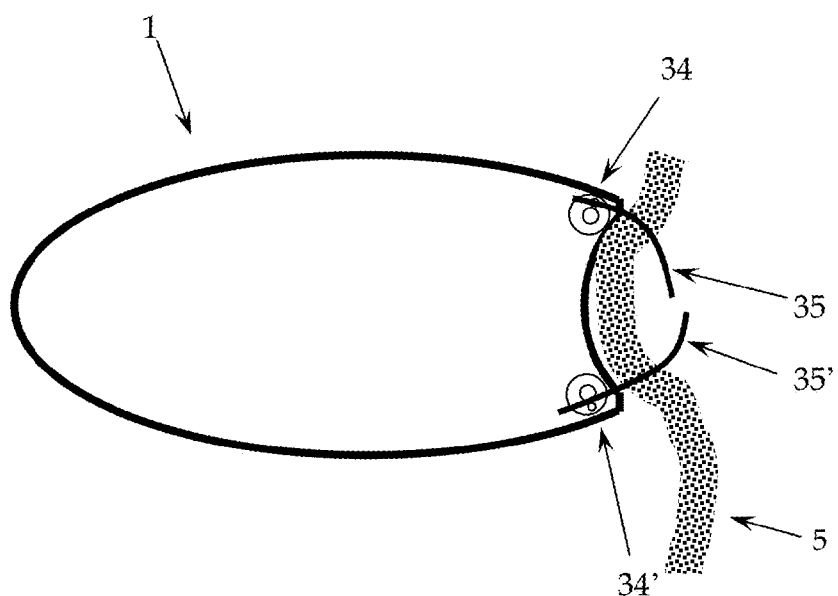
FIG. 4B is a schematic view of an in-vivo medical device comprising the two wires "earring" mechanism after anchoring to the tissue of the GI tract wall, in accordance with an embodiment of the present invention.

In some embodiments, the earring mechanism may comprise, for example, two wires (or earring catches) 35 and 35' and two electromotors 34 and 34', as depicted on FIGS. 4A and 4B, which schematically show the device 1 with such double earring mechanism, before and after anchoring to the tissue of the GI tract wall, respectively. The two wires 35 and 35' may be extended from openings 38 and 38', respectively, at opposing ends of the diameter of device 1. A different number of wires and/or electromotors may be used.

Figure 5A:
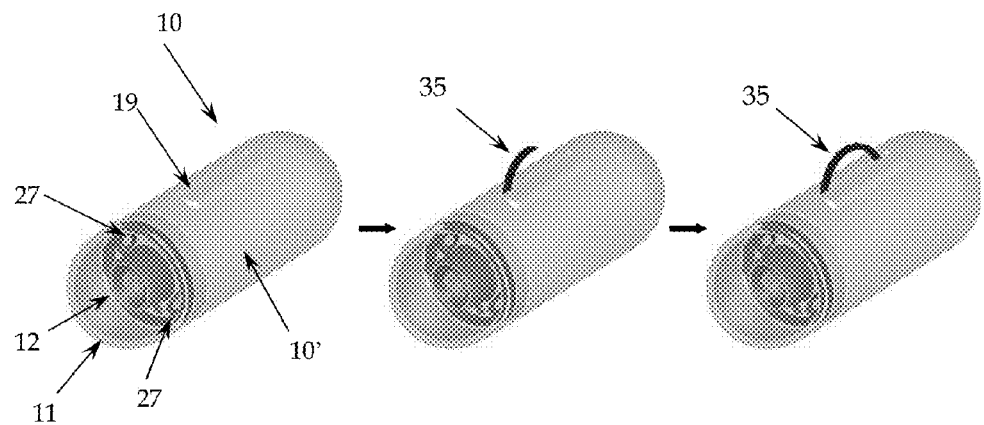
FIG. 5A is a perspective view of an in-vivo medical device comprising the "earring" mechanism at progressive stages of its operation, in accordance with one embodiment of the present invention.
Figure 5B:
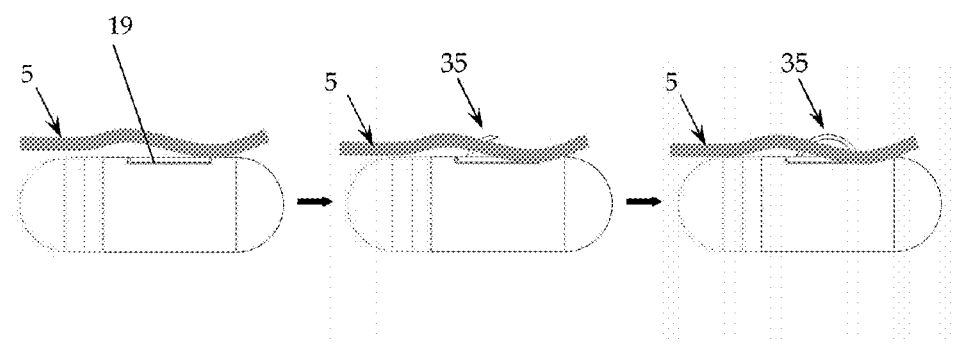
FIG. 5B is a schematic illustration of an in-vivo medical device comprising the "earring" mechanism at progressive stages of its operation anchoring the device to the tissue of the GI tract wall, in accordance with an embodiment of the present invention.
Figure 5C:
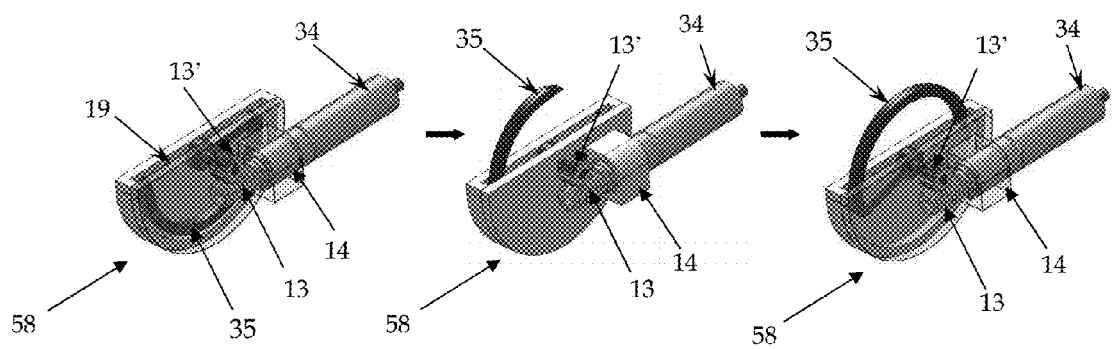
FIG. 5C is a perspective view of the "earring" mechanism at progressive stages of its operation, in accordance with one embodiment of the present invention.

Reference is now made to FIGS. 5A, 5B and 5C, which illustrate the earring mechanism. The progressive views of an in-vivo medical device with the earring mechanism are shown in a perspective view in FIG. 5A, in accordance with an embodiment of the present invention.

As shown in FIG. 5A, all the components of the in-vivo device 10 are substantially contained within housing 10', which may or may not be transparent. The housing 10' may, for example, have the following dimensions: 5-12 mm in width and 10-32 mm in length, although other dimensions are possible. The walls of housing 10' may be made of any suitable biocompatible polymeric material, such as polycarbonate, polystyrene, parylene, parylene C and isoplast, and may taper or may be substantially parallel as shown in FIG. 5A. In other embodiments, the walls of housing 10' may have any other suitable shape.

The earring mechanism may be located in a special chamber 58 (shown in FIG. 5C) formed within the housing 10' and generally sealed from the internal components of the device 10. This chamber 58 may have an earring slot 19 through which earring catch 35 may emerge to outside device 10. The earring slot 19 may be covered with a film cover, which the earring catch 35 breaks as it moves through slot 19. When the device is pressed against tissue 5 of the GI tract wall, as shown in FIG. 5B, the motor operated earring catch 35 may be extended from earring slot 19 and anchor the device 10 to the tissue of the GI tract wall.

In one embodiment, the earring mechanism may comprise earring catch 35, electromotor 34 and gear 14, as shown in FIG. 5C. Earring catch 35 may be placed at and extended from a side wall of the in-vivo device 10, such as the cylindrical portion of the housing 10' of the elongated or capsule-shaped medical device 10 for "parallel" docking. Alternatively, earring catch 35 may be placed at and extended from one of the ends of the capsule-shaped or elongated medical device 10 (similar to the position shown in FIGS. 3A to 4B), thus anchoring the device such that it is perpendicular to the surface of the tissue. Gear 14 may cause worm drive 13 to rotate, which then causes worm gear 13' to rotate, since worm gear 13' meshes with worm drive 13. Once worm gear 13' rotates, it may rotate against earring catch 35 to which it is connected, such that earring catch 35 may extend from slot 19 (FIGS. 5B-5C).

In yet a further embodiment, the earring catch 35 may have a pointed head or tip capable of piercing the tissue 5 of the GI tract walls. Catch 35 may have any cross-sectional size and shape that may firmly hold the in-vivo device in place. For example, it may have a diameter of about 0.5 to 2 mm, although other diameters are possible.

The earring catch 35 may be formed of any biodegradable material strong enough to hold the in-vivo device anchored in place but which may be dissolvable in the liquid environment of the GI tract. Suitable materials are, for example, caramel, biodegradable plastic resins or starches, such as gelatin, or wax. After a period of time, at least the pointed head of the earring catch 35 may dissolve, thus releasing the in-vivo device 10 from the tissue 5 of the GI tract wall. The device 10 may thereby continue moving through the GI tract.

In another embodiment, catch 35 may be formed of a non-biodegradable material strong enough to hold the in-vivo device anchored in place, such as stainless steel, Nitinol, Titanium, Zirconia or biocompatible polymers. Earring catch 35 may be retracted back into slot 19 by an operator command triggering electromotor 34 to rotate gear 14 in backwards (reverse) direction, and thereby releasing the in-vivo device 10 into the GI tract upon completion of the diagnostic or therapeutic procedure. In other embodiments, release of device 10 need not comprise the earring catch 35 being retracted back into slot 19, but rather release of the device 10 may occur after a time period in which the tissue that device 10 is anchored to becomes necrotic. The pinned tissue may become necrotic after a few days, and the in-vivo device 10 may detach itself from the tissue and thus be naturally discharged.

According to some embodiments, imaging head 12 of the device shown on FIG. 5A may include one or more illumination sources 27, such as LEDs or other suitable illumination sources, and lenses placed behind a transparent convex (e.g., dome-shaped) optical window 11 of the device.

Figure 6A:
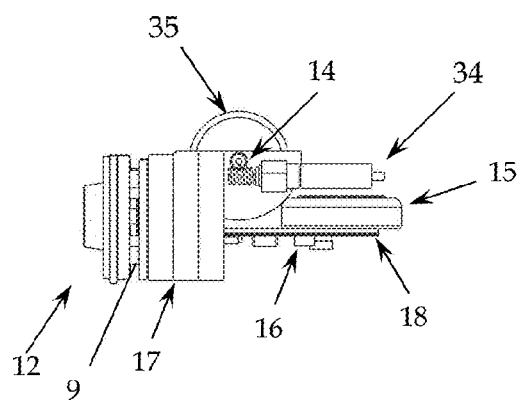
FIGS. 6A-6C illustrate schematic views of the internal components of the in-vivo medical device comprising the "earring" mechanism, in accordance with an embodiment of the present invention.
Figure 6B:
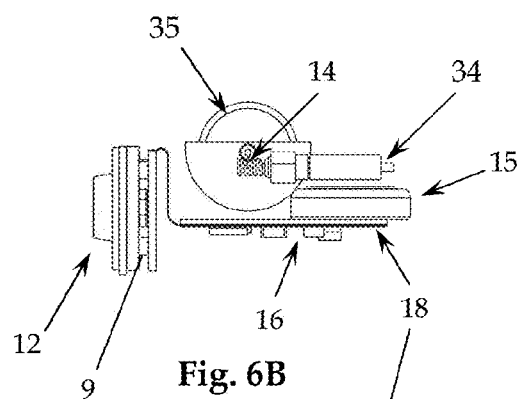
Figure 6C:
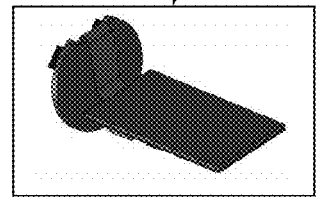

Reference is now made to FIGS. 6A-6C, which schematically illustrate an assembly of components of an in-vivo medical device 10 having an earring mechanism. Imaging head 12 of the in-vivo device may include an in-vivo camera/imager setup 9 including one or more illumination sources 27 (shown in FIG. 5A) in order to acquire an in-vivo image of a body lumen. These illumination sources 27 may, for example, illuminate a body lumen or cavity being imaged and/or sensed. An optical system (not shown), including, for example, one or more optical elements, such as one or more lenses or composite lens assemblies, one or more suitable optical filters, or any other suitable optical elements, may be included in the in-vivo device 10 and may aid in focusing reflected light onto an imager 9, focusing illuminated light, and/or performing other light processing operations.

In a further embodiment, the in-vivo device 10 may include the earring mechanism (shown in FIG. 5C) comprising earring catch 35, electromotor 34, worm drive 13, worm gear 13' and gear 14, as described in more detail hereinabove.

In another embodiment, the components of the device are placed on a multilayered imaging and sensing printed circuit board, such as rigid-flex printed circuit board (PCB) 18, for sensing the current location, for steering and orienting the in-vivo device, and for transmitting corresponding location and orientation data to an external system that generates the external magnetic fields.

The PCB 18 may include circuitry for capturing images, for example, of the GI tract, and for transmitting images to an external data recorder. The PCB 18 may also include a sensing coil assembly ("SCA") for sensing electromagnetic fields in order to facilitate sensing of a current location and/or current orientation and/or angular position of the in-vivo device. The SCA, which may be part of the magnetic steering unit (MSU), may include one or more electromagnetic field sensing coils, which may be disposed, for example, on one or more PCBs. Further, the SCA may include a magnetic field sensing ("MFS") section that may have embedded or formed therein some of the electromagnetic field sensing coils; other one or more electromagnetic field sensing coils may be included or formed in other sections of the PCB 18 that may be structurally separated from the MFS section.

The PCB 18 may additionally include an antenna, typically associated with a transmitter for wirelessly transmitting data, e.g. images, from the device to an external receiver. The PCB 18 may further include electronics 16 and contact points to connect additional components.

The MSU may include a permanent magnets assembly 17 ("PMA") for interacting with the magnetic field to thereby produce a propelling force and/or a repelling force and/or a rotational force, for steering and rotating the device. Thus, the PMA 17 may include one permanent magnet or a set of permanent magnets. A permanent magnet may be a ring, or it may be annular or ring-like shaped.

In some embodiments, data collected or sensed by the in-vivo device of the invention, e.g., images and image data taken from the body lumen, may be transmitted by a transmitter (not shown) to an external receiver or recorder unit, which may be portable, non-portable, mobile, non-mobile, wearable, or the like.

The components of the in-vivo diagnostic device may receive power from a power source 15, which may take the form of internal batteries, power cells, or power circuitry such as a wireless power receiving unit based on RF power transmission, which may be included in the device. The battery within the power source 15 may be very small. An example of a suitable battery may be a silver oxide battery often used to power watches, lithium batteries or any other suitable electrochemical cells having a high energy density. The battery may, for example, have voltage of 1.55 volts and a capacity of 12.5 mA-hours and may have a disk-like shape with a diameter of approximately 5.7 mm and a thickness of approximately 1.65 mm, though other dimensions and shapes may be used. With a typical range of power requirements, the battery may be expected to power the in-vivo device for between approximately two weeks and eighteen months, depending on actual usage conditions. Other suitable power sources may be used. For example, power source 15 may receive power or energy from an external power source (e.g., an electromagnetic field generator), which may be used to transmit power or energy to the in-vivo diagnostic device.

In a further embodiment, power source 15 may be rechargeable via induction or ultrasonic energy transmission, and may include an appropriate circuit for recovering transcutaneously received energy. For example, power source 15 may include a secondary coil and a rectifier circuit for inductive energy transfer. In still other embodiments, power source 15 may not include any storage element, and the in-vivo device may be fully powered via transcutaneous inductive energy transfer. As an example, such power source is commercially available from Medtronic, Inc. of Minneapolis, Minn.

Figure 7A:
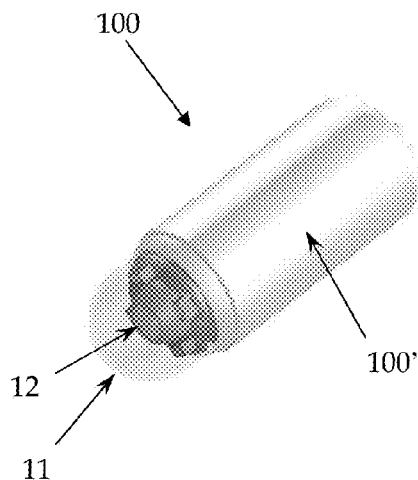
FIG. 7A is a perspective front view of an in-vivo medical device with the "snap" mechanism, in accordance with one embodiment of the present invention.
Figure 7B:
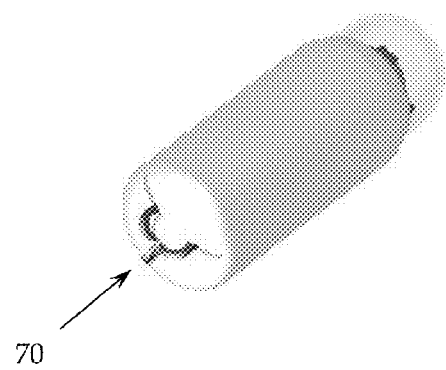
FIG. 7B is a perspective back view of the in-vivo medical device with the "snap" mechanism, in accordance with one embodiment of the present invention.
Figure 7C:
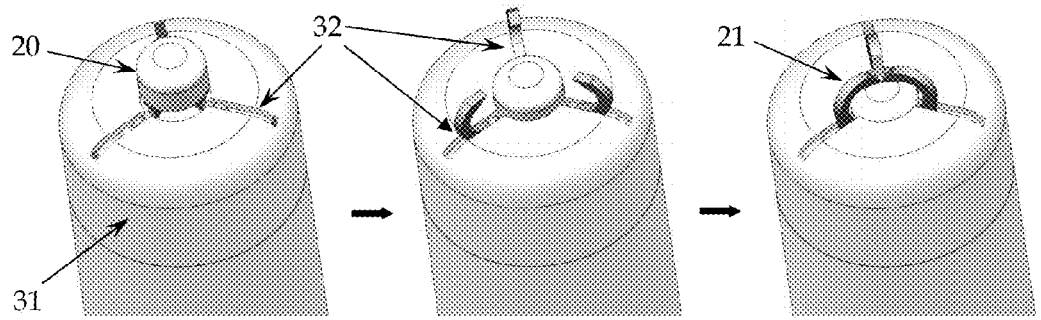
FIG. 7C illustrates perspective back views of the in-vivo medical device comprising the "snap" mechanism before, during and after anchoring the device to the tissue of the GI tract wall, in accordance with an embodiment of the present invention.
Figure 7D:
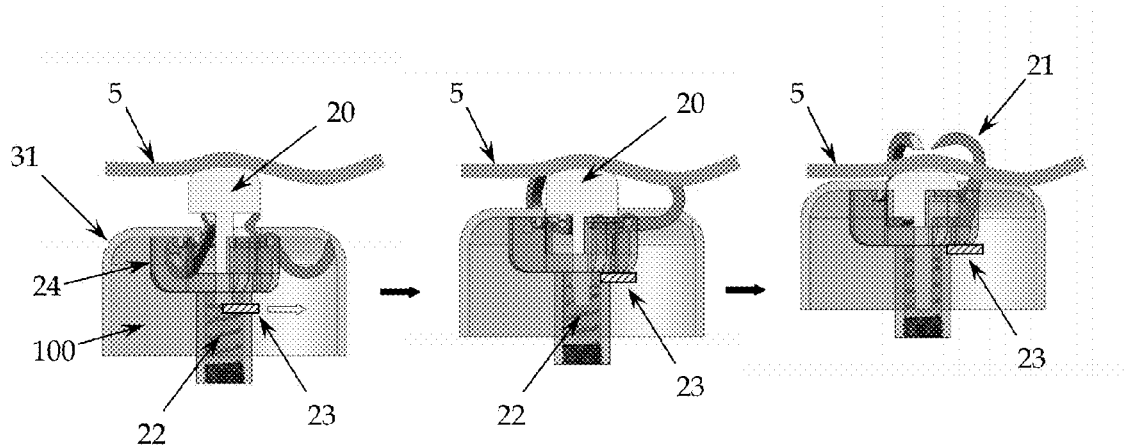
FIG. 7D illustrates schematic cross-sectional views of the in-vivo medical device comprising the "snap" mechanism before, during and after anchoring the device to the GI tract wall tissue, in accordance with one embodiment of the present invention.

Reference is now made to FIGS. 7A-7D and 8A-8B showing the "snap" mechanism 70 and an in-vivo medical device 100 comprising the same, according to an embodiment of the present invention. In a particular embodiment, the "snap" mechanism is based on a two-step process initiated by release of a special safety catch 23 when a forcer (push-button) 20 is pressed against the wall of the GI tract, as shown in FIG. 7D.

In one embodiment, the retraction (or release) of safety catch 23 may be triggered externally by an operator activating the magnetic control inside the device. The safety catch 23 may then represent, for example, an electromagnet comprising a cylindrical ferromagnetic core element surrounded by electrically conductive coil of the solenoid assembly, which is a part of the retraction and release mechanism.

In another embodiment, the release of safety catch 23 may be triggered internally by a permanent magnets assembly activated by touching sensors, as described above (FIG. 1A). As a result, housing 100' of the in-vivo device 100 moves towards the tissue 5 of the GI tract wall, pushing forcer 20 back (down/inwards) into stationary forcer base 24. Consequently, forcer 20 compresses spring 22 (shown in FIG. 7D) and small teeth 29 of grippers 21 (shown in FIG. 8B), are then fastened to ring 30 (FIG. 8B). The grippers 21, which are initially held open, rapidly snap shut under pressure of the forcer 20 catching the GI tract wall tissue 5.

As shown on FIGS. 7C, 7D and 8A, the snap mechanism may be located in chamber 31 formed within the housing 100' and sealed from the internal components of device 100. The chamber 31 may have a number of slots (openings) 32 through which grippers 21 extend from chamber 31. The slots 32 may typically be covered with a film cover, which the grippers 21 break as they move through their respective slots 32.

As shown in FIGS. 7B and 7C, the chamber 31 with the snap mechanism 70 may be located at the back end of the elongated in-vivo device 100, thus anchoring device 100 by its back end to the GI tract wall. That is, when chamber 31 is located at the back end of device 100, snap mechanism 70 is anchoring the device 100 such that the longitudinal axis of housing 100' is perpendicular to the GI tract wall. Alternatively, chamber 31 may be located at the side of the device housing 100', parallel to the longitudinal axis of device 100, thus anchoring the device by the side to the GI tract wall, i.e., such that the longitudinal axis of housing 100' of device 100 is parallel to the GI tract wall.

In a particular embodiment, grippers 21 may have pointed heads capable of pinching the tissue of the GI tract walls. Such pointed heads may have any size and shape which may firmly hold the in-vivo device in place. For example, each pointed head may have a diameter at its point of about 0.5 to 2 mm, although other dimensions may be implemented.

As the aforementioned earring catch, grippers 21 may also be formed of any biodegradable material strong enough to hold the in-vivo device anchored in place but which may be dissolvable in the liquid environment of the GI tract. Suitable materials are the same, for example, caramel, biodegradable plastic resins or starches, such as gelatin, or wax. After a period of time, at least the pointed head of grippers 21 may dissolve, thus releasing the in-vivo device into the GI tract. Alternatively, grippers 21 may be formed of a non-biodegradable material, strong enough to hold the in-vivo device anchored in place, e.g., stainless steel, Nitinol, Titanium, Zirconia or biocompatible polymers. According to some embodiments, grippers 21 may be retracted back into slots 32 by an operator command applying magnetic force to safety catch 23 in order to move it back and thereby release spring 22. The released spring 22 pushes forcer 20 to go up, open the grippers 21 and release the in-vivo device 100 into the GI tract.

In some embodiments, the grippers 21 need not be retracted back into slots 32 in order to release device 100 from the gripped tissue. Instead, the gripped tissue may become necrotic after a few days, and the in-vivo device 100 may detach itself from the tissue and thus be naturally discharged.

Figure 9A:
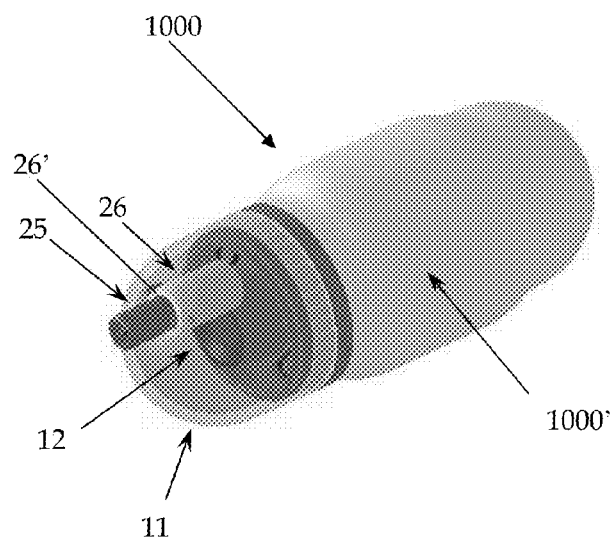
FIG. 9A is a perspective view of an in-vivo medical device with the "harpoon" mechanism, in accordance with one embodiment of the present invention.
Figure 9B:
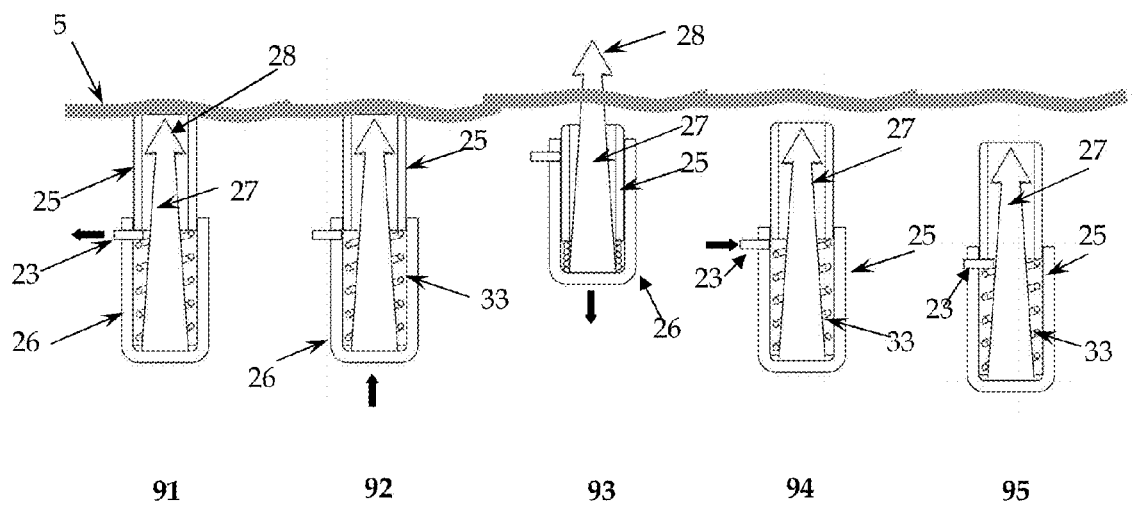
FIG. 9B illustrates progressive schematic cross-sectional views of the "harpoon" mechanism before, during and after anchoring the device to the tissue of the GI tract, in accordance with an embodiment of the present invention.

Reference is now made to FIGS. 9A and 9B showing an in-vivo medical device 1000 comprising a harpoon and a harpoon mechanism, respectively. In a particular embodiment, the harpoon mechanism is located within chamber 26 formed within housing 1000' and generally sealed from the internal components of the in-vivo device 1000. Chamber 26 may comprise an opening 26' through which cover 25 moves back and forth, uncovering and covering harpoon 27, respectively.

Harpoon 27 may have an arrowhead 28 (shown in FIG. 9B) capable of piercing the GI tract walls. The arrowhead 28 may have any size that can hold the in-vivo device 1000 in place. For example, the arrowhead 28 may have a diameter, at the widest part of the arrow, of 0.5-2 mm. Spring 33, which is typically formed of any spring-like material, may force the cover 25 substantially all the way through the chamber 26 and against tissue 5 of the GI tract walls in order to cover harpoon 27 and release the device 1000, once the diagnostic or therapeutic procedure is completed.

Reference is now made to FIG. 9B schematically showing the harpoon mechanism. The first step (91) is the release of safety catch 23, which may be triggered either externally, by an operator command, or internally by a permanent magnets assembly activated by touching sensors, as described above (FIG. 1A). Once safety catch 23 is released, the device may be pulled by external magnetic field towards tissue 5 of the GI tract wall, as shown in FIG. 9B, second step (92). As a result, in the third step (93), cover 25 is pushed down, moves back into chamber 26, and uncovers harpoon 27. The uncovered harpoon 27 pierces tissue 5 of the GI tract wall, thereby anchoring the device 1000 to the wall. Spring 33 is simultaneously pressed by cover 25 and held under pressure during the entire diagnostic or therapeutic procedure, since the anchoring of the device 1000 does not allow spring 33 to expand.

As in the case of the aforementioned earring catch and snap grippers, harpoon 27 may also be formed of any biodegradable material strong enough to hold the in-vivo device in place but which may be soluble in the liquid environment of the GI tract. Suitable materials may be, for example, caramel, biodegradable plastic resins or starches, such as gelatin, or wax. After a period of time, at least the arrowhead 28 of harpoon 27 may dissolve, thereby releasing the in-vivo device to continue moving through the GI tract. In other embodiments, harpoon 27 may be formed of a non-biodegradable material strong enough to hold the in-vivo device in place, e.g., stainless steel, Nitinol, Titanium, Zirconia or biocompatible polymers. In some embodiments, the pierced tissue may become necrotic after a few days, and the in-vivo device 1000 may detach itself from the tissue and thus be naturally discharged.

In another embodiment, as shown in FIG. 9B, fourth step (94), cover 25 may be pushed forward by retracted spring 33 against tissue 5 of the GI tract walls and thus cover harpoon 27. The operator may then apply magnetic force to safety catch 23 in order to move cover 25 back into housing 1000' and hold spring 33 in a released configuration. As a result, the in-vivo device may be released into the GI tract, as shown in FIG. 9B, final step (95).

In general, release of the earring catch 35, grippers 21 and harpoon 27 is possible in one of the following ways: by the gripped tissue becoming necrotic; by dissolution of catches, grippers or harpoons that are made of dissolvable material; or by disengagement command and corresponding retraction mechanism.

In some embodiments, catches, grippers and harpoons (hereinafter, the "anchors"), described above, may additionally serve as drug delivery units made of a composition comprising a biodegradable material and a pharmaceutical drug. For example, the drug might be an antibiotic to counter possible injury caused by the hooks when they are pinched or pierced into the tissue of the GI tract wall.

In another embodiment, the pharmaceutical drug might be a drug needed at a specific location of the GI tract. In this embodiment, the location, such as pathological lesion 4 (shown in FIGS. 3A and 3B), may be known or detected in-vivo, and an external operator may instruct the device at the appropriate moment to dock the device at the desired location, as explained above, and to cause the anchors to jab the tissue of the GI tract wall.

In yet a further embodiment, the biodegradable composition of the anchors may comprise at least one marker or any other compound needed to be delivered, preferably in a site specific manner, to a body lumen.

In general, as noted above, the anchoring mechanisms may be located at the back end of the in-vivo device, thus anchoring the device by its back end to the GI tract wall, causing the longitudinal axis of the device to be positioned perpendicularly to the GI tract wall. Alternatively, the anchoring mechanisms may be located at the side of the device's housing parallel to the longitudinal axis of the device, thus anchoring the device by its side to the GI tract wall, thereby causing the longitudinal axis of the device to be placed parallel to the GI tract wall. The desired tools and devices needed for diagnostic and therapeutic procedures, in particular, the imaging setup, may be conveniently mounted at the convex dome end, as shown in FIGS. 5A, 7A and 9A.

In some embodiments, the in-vivo medical device may include one or more sensors, which may, for example, sense, detect, determine and/or measure one or more values of properties or characteristics of the surrounding of the device. For example, the device may include a pH sensor, a temperature sensor, an electrical conductivity sensor, a pressure sensor, or any other known suitable in-vivo sensor.

Figure 10:
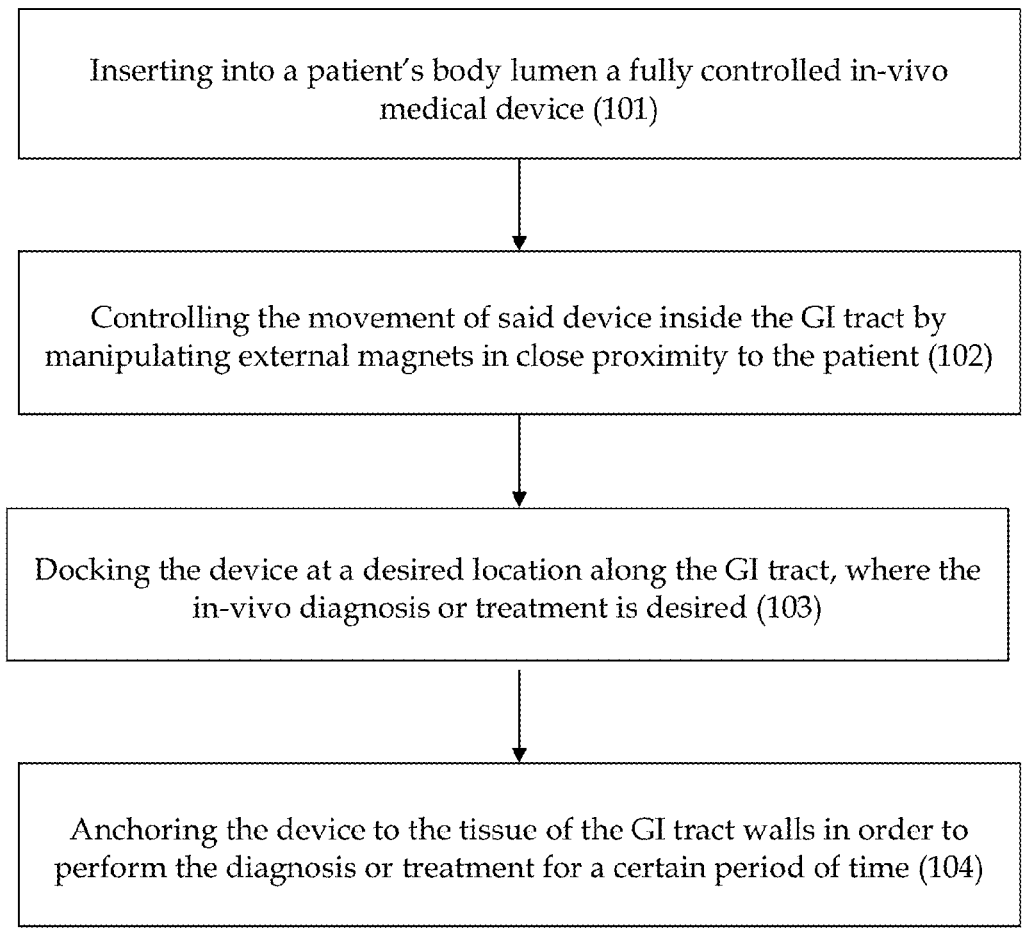
FIG. 10 is a flow chart describing the method for anchoring the in-vivo medical device, in accordance with an embodiment of the present invention.

Reference is now made to FIG. 10, which shows a flow chart describing a method for anchoring the in-vivo medical device according to embodiments of the present invention. According to some embodiments, the in-vivo diagnostic method may include the following steps:

inserting into a patient a fully controlled in-vivo medical device, e.g., either one of devices 1, 10, 100 or 1000 (101);

controlling the movement of said device inside the GI tract by manipulating external magnets in close proximity to the patient (102);

docking the device at a desired location along the GI tract, where the in-vivo diagnosis or treatment is desired (103); and anchoring the device to the tissue of the GI tract walls in order to perform the diagnosis or treatment for a certain period of time (104).

The in-vivo diagnostic device (e.g., device 1, 10, 100 or 1000) may be inserted into a body lumen, for example, into a patient's GI tract, e.g., by swallowing, by using a delivery device or by any other insertion means or methods. The method may further optionally include acquiring in-vivo images of the body lumen or acquiring other in-vivo data, e.g., pH, pressure, temperature, etc.; transmitting the acquired in-vivo images or other data; analyzing the in-vivo image or other data; and/or performing other suitable operations.

According to a specific embodiment, a system for anchoring the device may comprise the fully controlled medical in-vivo device, external rotatable magnets for steering the internal magnets of said device thereby fully controlling its movement inside the GI tract, an external receiver/recorder able to receive data (e.g., image data) transmitted by the in-vivo device, and a computing platform or workstation able to steer and control the device, and to store, process, display, or analyze the received data.

Various aspects of the various embodiments disclosed herein are combinable with the other embodiments disclosed herein. Although portions of the discussion herein may relate to three specific anchoring mechanisms (i.e. earring, snap and harpooning), embodiments of the invention are not limited in this regard, and may include, for example, other available mechanisms and tools for anchoring the in-vivo medical device.

Figure 11:
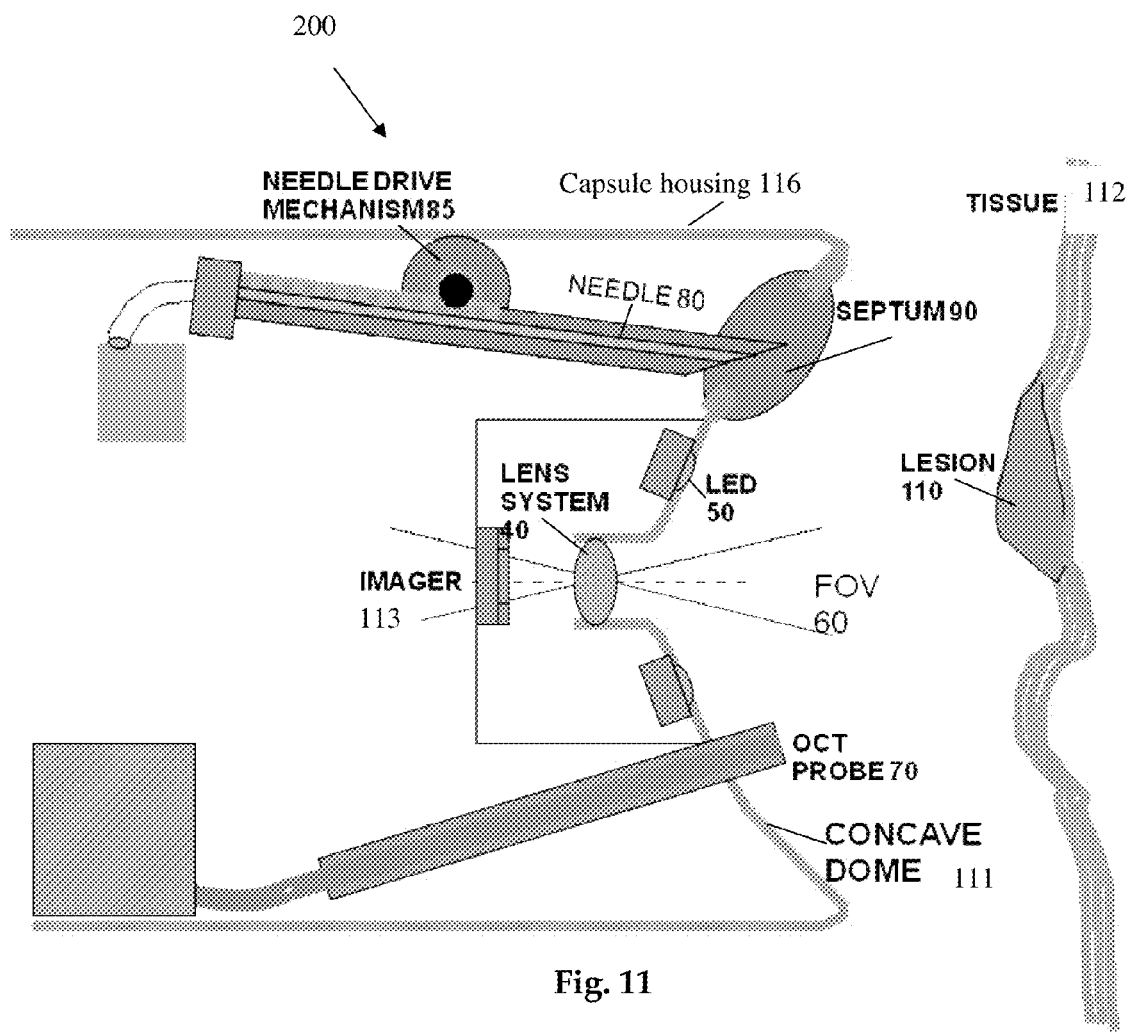
FIG. 11 illustrates a schematic view of an in-vivo medical device comprising a concave window, in accordance with one embodiment of the present invention.

Reference is now made to FIG. 11, which illustrates a schematic view of an in-vivo medical device comprising a concave window, in accordance with one embodiment of the present invention. In-vivo medical device 200 may comprise a concave shaped window 111 that may be positioned at one end of elongated housing 116 of device 200. A concave shaped window, such as concave window 111, may enable better imaging of small areas as compared to a device with a convex window. A device with a concave window may enable a sensing or imaging mechanism within device 200 to get closer to an area of interest, e.g., a polyp, than a sensing or imaging mechanism within a device with a dome shaped window, since the convex or dome window creates a distance between the tissue and the imager that is in encapsulated within the device. A closer view of an area of interest may enable acquisition of an image with higher resolution. Furthermore, when a device, e.g., device 200 comprises a concave window 111, a lesion 110 of a small size may substantially fit within the void created by the concave window 111. Once the device 200 is set around the site of interest, tools may be ejected from the concave window 111 in order to treat or examine the site of interest.

In some embodiments, device 200 may comprise illumination sources 50, e.g., LEDs, for illuminating the tissue in-vivo. In some embodiments, device 200 may comprise at least two illumination sources, although other numbers of illumination sources may be used. Device 200 may further comprise an image sensor 113 for acquiring in-vivo images and optical system 40 for focusing light reflected off the tissue onto the image sensor 113. In some embodiments, imager 113 may be located at the apex of the concave window 111, whereas in other embodiments, the imager 113 may be located more to the sides of the concave window, in proximity to the location of the LEDs 50.

In some embodiments, the remaining surface of the concave window 111 may be used as support for a variety of tools for either treatment or diagnosis while the device 200 is in-vivo. FIG. 11 illustrates two examples of tools that may be implemented in device 200, as discussed below.

For example, device 200 may comprise a needle 80 to be used either for medication administration, or as a suction tube for drawing in-vivo fluids into the device 200 for later examination, or even for antibody dispensing in order to mark proteins that may indicate on various pathologies in-vivo. Needle 80 may be driven by a miniature motor 85 and may be protected and covered by a self sealing biocompatible septum 90, which is located on the surface of concave window 111. Once an operator identifies that the device 200 is positioned in close proximity to a lesion, e.g., lesion 110, the operator may send an operational command to the motor 85 to begin driving the needle 80 through septum 90 and outside concave window 111.

The needle 80 may inject medication to the lesion 110 or the lesion area. In other embodiments, the needle 80 may draw fluids from the lesion 110 or from its surroundings; either from the tissue surrounding the lesion 110 or from the fluids flowing nearby the lesion. In other embodiments, needle 80 may be used to inject preselected antibodies into the tissue 112 or specifically into lesion 110. The preselected antibodies may be selected according to the pathology sought. For example, if colorectal cancer is to be screened for by device 200, appropriate antibodies that bind to colorectal cancer biomarkers (proteins exhibited on the surface of the tissue or secreted by cells that exhibit pathology, e.g., colorectal cancer) may be inserted into device 200 and may be injected by needle 80.

In some embodiments, needle 80 may further be used for injecting a marking agent for marking a pathology by coloring it. The needle 80 may inject the color onto the tissue such that the entire area that is proximate to the needle 80 may be colored. However, in other embodiments, the marking may be specific to pathological areas only such that, for example, the marking agent may include antibodies that would cause coloring only to tissue that includes biomarkers to a pathology, e.g., lesion 110.

In some embodiments, once injection/withdrawal of the substance into/from the lesion 110 or the lesion area has been completed, needle 80 may be retracted backwards towards the inside of device 200 by motor 85, at the end of either one of the procedures described above.

In some embodiments, device 200 may comprise (either in addition to needle 80 or instead of needle 80) an Optical coherence tomography (OCT) probe 70. OCT probe 70 may be capable of imaging sub mucosal tissue. In some embodiments, OCT probe 70 may comprise a septum, similar to septum 90, and may further comprise a driving mechanism, similar to motor 85. Other optical tools may be used, e.g., a spectral sensor or a fluorescence sensor. In some embodiments, such optical sensors may require spectral illumination, such that some of illumination sources 50 may illuminate in white light, whereas some of illumination sources 50 may illuminate in narrow band wavelengths suitable for spectral imaging. OCT probe 70, or any other probe that may be implemented in device 200, may be retracted backwards into device 200 subsequent to end of the operation of the probe.

Either of needle 80 or probe 70, as illustrated in FIG. 11, may be implemented in device 200 alone or in combination with the other tool. Other tools may be used.

Reference is now made to FIG. 12, which illustrates a schematic view of an in-vivo medical device comprising a concave window, in accordance with a second embodiment of the present invention. Device 300 may comprise a concave window 311. In some embodiments, concave window 311 may comprise a mini-convex shaped window 312 typically located at the center of the concave window 311. Mini-convex window 312 may typically be used as a lens that focuses light reflected off a tissue and onto imager 313. Imager 313 may be placed behind the mini-convex window 312. A mini-convex window 312 may be used for avoiding full contact between the tissue and the window 311. When the tissue is very close to the imager (e.g., imager 313) it may be difficult to acquire an image of the tissue, as substantially no light is able to reflect off the tissue and reach imager 313. By creating some distance between an area of the tissue, e.g., a lesion (for example lesion 110 in FIG. 11) a bright and detailed image of the tissue may be acquired by imager 313.

According to some embodiments, any of the tools that may be implemented as part of device 200 may be implemented as part of device 300 as well, alone or in combination with others.

Reference is now made to FIGS. 13A-B, which illustrate a schematic view of an in-vivo medical device comprising a concave window, and the tissue following operation of the device, respectively, in accordance with a third embodiment of the present invention. Device 400 may comprise a concave window 411 to enable a sensing or imaging mechanism within the device 400 to get close to a site of interest, e.g., to a lesion 410. Device 400 may further comprise a mini-convex window 412 (similar to mini-convex window 312 in FIG. 12). Device 400 may comprise an imager 413, which may be typically positioned behind the mini-convex window 412. Device 400 may also comprise illumination sources 450 that may be placed on both sides of the imager 413 as well as the mini-convex window 412.

According to some embodiments, device 400 may comprise a polyp snaring mechanism. The polyp snaring mechanism may comprise a motor screw drive 442, a moving cover or jacket 441 that may move back and forth along the housing 400' of device 400, and stretched bands 440. Once an operator of device 400 spots a polyp, e.g., polyp 410 by viewing images acquired by imager 413, the operator may operate the device 400 to move towards the polyp 410 (by rotating external magnets, as described in FIGS. 1A-1B) such that concave window 411 is substantially covering the entire polyp 410. The operator may then send a command to the motor 442. Motor 442 may push moving cover 441 forward towards the end of the elongated housing that comprises the concave window 412. Bands 440 that may be stretched around the periphery of housing 400' and which are typically positioned proximally to the end of the housing 400' where the concave window 412 begins may then be pushed forward by the moving cover 441. Once a stretched band 440 is pushed forward by the moving cover 441, it soon reaches the end of housing 400' and is in fact pushed off of housing 400', and off of concave window 411 onto polyp 410. After it is pushed off device 400, the stretched band 440 may return to its initially small diameter that it had prior to being stretched over housing 400'. Thus, at the end of the procedure polyp 410 may be a snared polyp 410' that is caught by band 440, as shown in FIG. 13B.

In some embodiments, bands 440 may be made of an elastic material such as rubber, silicon, or any other stretchable material, whose resting (contracted) length is small enough to ensnare a polyp 410 but whose stretched length is large enough to fit around the periphery of housing 400'. In some embodiments, more than one band 440 may be attached onto housing 400', so as to enable multiple polyps being snared throughout the entire procedure, while using the same device 400. Once a first band is pushed off device 400, the second band takes the place of the first band, i.e., the second band comes closer to the end of housing 400', where the first band was located before being pushed off device 400.

In some embodiments, the polyp snaring mechanism, as described above, may be incorporated at the distal end (i.e., operating and/or imaging end) of an autonomous in-vivo device, e.g., swallowable capsule endoscope 400. In other embodiments, a polyp snaring mechanism, as described above, may be incorporated at the distal end of any of the following devices: conventional endoscopes, laparoscopes, or any similar invasive or minimally invasive device.

Figure 14:
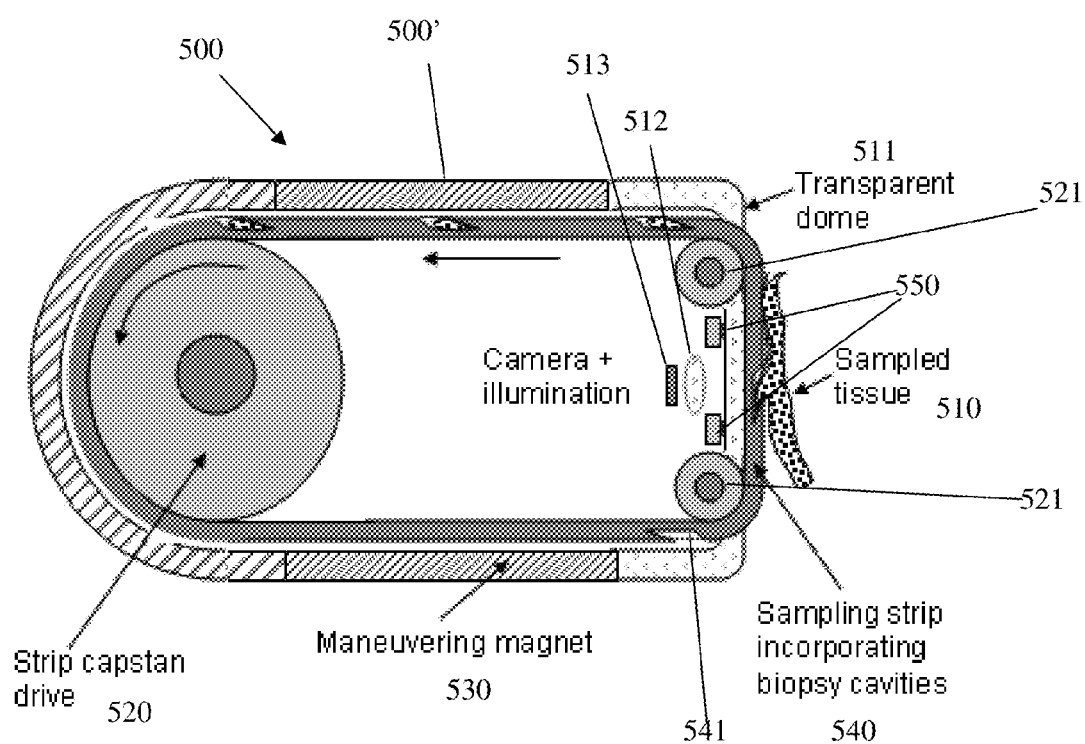
FIG. 14 illustrates a schematic view of an in-vivo medical device in accordance with an embodiment of the present invention.

Reference is now made to FIG. 14, which illustrates a schematic view of an in-vivo medical device in accordance with an embodiment of the present invention. Device 500 may comprise a transparent window 511 which may have a substantially flat shape or may have a convex shape. Device 500 may further comprise illumination sources 550 that may illuminate tissue 510 located externally to device 500. Device 500 may comprise an imager 513 for imaging the tissue 510 and its surroundings. Device 500 may comprise an optical system 512 for focusing the light reflected off the tissue onto the imager 513. Optical system 512 may comprise lenses as well as other optical elements. In some embodiments, optical system 512 and imager 513 may be positioned substantially at the center of window 511, while illumination sources 550 may be located on the sides of imager 513. In other embodiments, other positioning may be used.

In some embodiments, device 500 may comprise a tissue sampling mechanism. The tissue sampling mechanism may comprise a sampling strip 540 that may include cavities 541 for tissue biopsy acquisition. At least part of each of cavities 541 may be sharp so as to cut off a sample of a tissue, e.g., tissue 510 (located externally and in close proximity to device 500). The tissue sample may later be examined to determine whether the tissue is cancerous or benign. In order for device 500 to come in contact with the tissue, e.g., tissue 510, and then acquire a tissue sample, device 500 may comprise a magnetic element 530 and along with applying external magnetic fields, device 500 may be magnetically maneuvered towards the tissue.

In some embodiments, sampling strip 540 may be maneuverable and may be turned by a drive wheel 520, which may be located at one end of the elongated device 500, opposite the end comprising window 511. Sampling strip 540 may further be turned by and/or around smaller wheels, e.g., wheels 521, which may be located at the end of device 500 comprising window 511. Typically, wheels 521 may comprise two wheels located one opposite the other, on both sides of window 511. Once drive wheel 520 and wheels 521 turn, either by a motor (not shown) or by the external magnetic fields, sampling strip 540 begins to turn around those wheels. Sampling strip 540 may comprise cavities 541, thus when sampling strip 540 is turned by the wheels one of the cavities 541 may be in contact with the tissue external to device 500, and a sample may be acquired. Once a tissue sample is acquired, the cavity 541 holding the sample enters housing 500' of device 500 and is kept inside, although it may be turned to a different location inside the housing as long as tissue samples are being acquired. In between sampling, strip 540 may be turned such that none of cavities 541 is in contact with the tissue external to device 500.

In some embodiments, once all cavities 541 are filled with tissue samples, e.g., tissue 510, the operator may cease operation of drive wheel 520 and of wheels 521, and thus all tissue samples are kept within housing 500'. After device 500 exits the body lumen, device 500 may be opened and the tissue samples may be extracted for pathological examination, which may determine presence of any malignant tissue in-vivo.

Sampling strip 540 may be made of, for example, stainless steel, as common in surgical knives. In other embodiments, other materials may be used. Although sampling strip 540 may typically be made of an opaque material, an image may still be acquired by imager 513, since sampling strip 540 need not block the entire area of window 511 but rather can block only a small fraction of the entire field of view.

A device, system and method in accordance with some embodiments of the invention may be used, for example, in conjunction with a device that may be inserted into a human body. However, the scope of the present invention is not limited in this regard. For example, some embodiments of the invention may be used in conjunction with a device that may be inserted into a non-human body or into an animal body.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An in-vivo medical device comprising:
   an image sensor;
   an optical system;
   at least one illumination source;
   a permanent magnet assembly interacting with external magnetic fields for generating magnetic forces for magnetically maneuvering said device to a desired location along a patient's GI tract; and
   an anchoring mechanism, wherein said anchoring mechanism is configured to attach said device to body tissue at the desired location for a period of time, said anchoring mechanism comprising:
   a chamber formed within a housing of said device, said chamber having an opening;
   a harpoon located within said chamber, at least a portion of said harpoon extending outside of said chamber, said harpoon configured to penetrate the body tissue;
   a harpoon cover configured to longitudinally move back and forth through said opening into said chamber and out of said chamber, respectively uncovering and covering said harpoon;
   a spring located within said chamber, said spring configured to hold said cover outside said chamber and covering said harpoon, and configured to allow said cover to be moved longitudinally back into said chamber; and
   a safety catch configured to prevent longitudinal movement of said cover unless released;
   wherein, when said safety catch is in place, said safety catch prevents said cover from moving from a position outside said chamber and covering said harpoon, and when said safety catch is released, said spring allows said cover to move longitudinally into said chamber through said opening when said cover is pressed longitudinally against the body tissue, thereby uncovering said harpoon and allowing said harpoon to penetrate the body tissue for anchoring the device to the body tissue.

2. The device according to claim 1, wherein said device is a swallowable self-contained capsule.

3. The device according to claim 1, wherein said device further comprises a power source.

4. The device according to claim 3, wherein said power source is one or more batteries.

5. The device according to claim 1, wherein said device comprises a closed loop docking control system.

6. The device according to claim 5, wherein said closed loop docking control system comprises a magnetic field generator, controlled by external magnetic fields, and one or more touch sensors transmitting a feedback signal to a control circuit, thereby indicating a proper contact of the device with the tissue of a GI tract wall.

7. The device according to claim 1, wherein said anchoring mechanism is triggered externally, by an operator.

8. The device according to claim 1, wherein said anchoring mechanism is triggered internally, by an automatic signal that is transmitted from a force threshold sensor or from a proximity sensor.

9. The device according to claim 1, wherein said anchoring mechanism is partially made of biodegradable material.

10. The device according to claim 1, wherein said anchoring mechanism is partially made of non-biodegradable material.

11. The device according to claim 1, wherein said chamber isolated from an interior of the device.

12. The device according to claim 1, wherein said device is an elongated device and wherein said anchoring mechanism is located at one end of the elongated device, thereby anchoring the device such that a longitudinal axis of the device is perpendicular to a GI tract wall.

13. The device according to claim 1, wherein said device is an elongated device and wherein said anchoring mechanism is located on the side of the device along the longitudinal axis of the device, thereby anchoring the device such that a longitudinal axis of the device is parallel to a GI tract wall.

14. The device according to claim 1, wherein said device comprises a concave window through which said image sensor, said optical system and said at least one illumination source operate.

15. A system for anchoring the in-vivo medical device of claim 1 to the walls of the GI tract, wherein said system comprises:
   said in-vivo medical device of claim 1;
   rotatable magnets, external to the device, for steering the permanent magnet assembly and thereby fully controlling the movement of the device inside the GI tract;
   an external receiver or recorder capable of receiving data, such as image data, transmitted by the device; and
   a computing platform or workstation able to control the steering and maneuvering of said device, and to store, process, display, or analyze the received data.

16. A method for anchoring the in-vivo medical device of claim 1 to the walls of the GI tract, wherein said method comprises the following steps:
   inserting into a patient said in-vivo medical device of claim 1;

controlling the movement of said device inside the GI tract by manipulating external magnets in close proximity to the patient;
docking said device at the desired location along the GI tract; and
anchoring said device to tissue of the GI tract walls for a period of time.

17. The method according to claim 16, wherein said method further comprises the steps of acquiring in-vivo images of the GI tract, transmitting the acquired in-vivo images, and analyzing the transmitted in-vivo images.

* * * * *